United States Patent
Sarac (10) Patent No.: US 8,439,188 B2
(45) Date of Patent: May 14, 2013

(54) METHOD FOR STORING A BIOABSORBLE MEDICAL DEVICE

(75) Inventor: Timur P. Sarac, Orange Village, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 387 days.

(21) Appl. No.: 12/717,977

(22) Filed: Mar. 5, 2010

(65) Prior Publication Data

US 2010/0300045 A1   Dec. 2, 2010

Related U.S. Application Data

(60) Provisional application No. 61/158,228, filed on Mar. 6, 2009.

(51) Int. Cl.
*B65D 81/24* (2006.01)
*A61B 17/06* (2006.01)
*A61F 2/04* (2006.01)

(52) U.S. Cl.
USPC ........... 206/210; 206/363; 206/438; 623/23.7

(58) Field of Classification Search ............ 206/63.3, 206/205–210, 438, 363; 623/2.1, 2.2, 23.7
See application file for complete search history.

(56) References Cited

U.S. PATENT DOCUMENTS

| | | | | |
|---|---|---|---|---|
| 4,182,446 | A * | 1/1980 | Penny | 206/205 |
| 5,007,533 | A * | 4/1991 | Purohit | 206/208 |
| 7,559,953 | B2 | 7/2009 | Sarac | |
| 7,699,168 | B2 * | 4/2010 | Ryan et al. | 206/438 |
| 7,967,138 | B2 * | 6/2011 | Ryan et al. | 206/438 |
| 2002/0120328 | A1 * | 8/2002 | Pathak et al. | 206/438 |
| 2003/0028255 | A1 * | 2/2003 | Hartig et al. | 623/23.7 |
| 2008/0128296 | A1 * | 6/2008 | Stopek et al. | 206/63.3 |
| 2008/0171972 | A1 * | 7/2008 | Stopek | 604/85 |
| 2008/0272012 | A1 * | 11/2008 | Stopek | 206/63.3 |
| 2009/0018633 | A1 * | 1/2009 | Lindquist et al. | 206/438 |
| 2010/0116694 | A1 * | 5/2010 | Stopek et al. | 206/210 |

* cited by examiner

*Primary Examiner* — Bryon Gehman
(74) *Attorney, Agent, or Firm* — Tarolli, Sundheim, Covell & Tummino LLP (57) ABSTRACT

A method is provided for storing a medical device. One step of the method includes providing a medical device having an initial tensile strength. The medical device is placed into a storage container so that at least a portion of the medical device is immersed in a hydrophobic liquid. Next, the medical device is stored in the storage container for a period of time. The initial tensile strength of the medical device is substantially preserved over the period of time.

12 Claims, 9 Drawing Sheets

METHOD FOR STORING A BIOABSORBLE MEDICAL DEVICE

RELATED APPLICATION

This application claims priority from U.S. Provisional Patent Application Ser. No. 61/158,228, filed Mar. 6, 2009, the subject matter of which is hereby incorporated by reference in its entirety.

TECHNICAL FIELD

The present invention relates generally to a method for storing a medical device, and more particularly to a method for storing a medical device to substantially preserve the tensile strength of the medical device.

BACKGROUND OF THE INVENTION

Open operative surgical treatment of arterial trauma has high morbidity and mortality, and can lead to lifelong disability. In 1991, stent grafts were developed as a minimally invasive way to treat arterial aneurysms. Despite numerous advances, however, stent graft placement in the lower extremities is often plagued by restenosis and thrombosis. Frequently, stents implanted in blood vessels restenose within 6 months after implantation, and the early thrombosis rate can vary between 5% and 27%. The restenosis rate of stents placed in long lesions (e.g., greater than 6 cm) in the superficial femoral artery has been as high as 78% after 12 months.

Percutaneous transluminal arterial angioplasty and stenting causes endothelium to denude, which consequently exposes underlying structural components (e.g., collagen, Von Willebrand factor, fibronectin, and laminin). Exposure of these structural components leads to platelet adherence, aggregation, and activation that can result in thrombus formation. Fibrin and platelets are deposited in stent struts early after implantation. If the endothelium does not reform over the stent struts and/or the structural components, this can lead to further arterial injury resulting in restenosis. Restenosis occurs when vascular smooth muscle cells undergo cell proliferation and migration with subsequent synthesis of extracellular matrix and collagen resulting in neointima formation. Neointimal formation is the major cause of restenosis and can cause in-stent stenosis within months.

Development of tissue-lined stent grafts for arterial occlusive disease is a new and exciting technology. Applying the tissue as the inner lining allows the body to recognize the tissue as its own, thus potentially reducing restenosis. Tissue-lined stents offer an attractive mechanism for quickly treating arterial injuries using minimally invasive techniques and eliminating the long-term sequelae of a foreign body. Tissue-lined stents, like all tissue products for the circulation (e.g., prosthetic pericardial heart valves), must be stored in appropriate preservative solutions (e.g., glutaraldehyde). Storage in such solutions, however, can lead to degradation and loss of tensile strength of the stent.

SUMMARY OF THE INVENTION

The present invention relates generally to a method for storing a medical device, and more particularly to a method for storing a medical device to substantially preserve the tensile strength of the medical device. According to one aspect of the present invention, a method is provided for storing a medical device. One step of the method includes providing a medical device having an initial tensile strength. The medical device is placed into a storage container so that at least a portion of the medical device is immersed in a hydrophobic liquid. Next, the medical device is stored in the storage container for a period of time. The initial tensile strength of the medical device is substantially preserved over the period of time.

According to another aspect of the present invention, a method is provided for storing a medical device. One step of the method includes providing a medical device having an initial tensile strength. The medical device is placed into a storage container so that at least a portion of the medical device is immersed in an anhydrous liquid. Next, the medical device is stored in the storage container for a period of about 2 weeks to about 8 weeks and then removed from the storage container. The initial tensile strength of the medical device is substantially preserved over the period of time.

According to another aspect of the present invention, a method is provided for storing a bioabsorbable polydioxanone (PDS) stent. One step of the method includes providing a bioabsorbable PDS stent having an initial tensile strength. The PDS stent is placed into a storage container so that at least a portion of the PDS stent is immersed in sterile mineral oil. Next, the PDS stent is stored in the storage container for a period of about 8 weeks. The PDS stent is then removed from the storage container. The initial tensile strength of the PDS stent is substantially preserved over the period of time.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Unless otherwise defined, all technical terms used herein have the same meaning as commonly understood by one of ordinary skill in the art to which the present invention pertains.

In the context of the present invention, the term "subject" can refer to any warm-blooded organism including, but not limited to, human beings, pigs, rats, mice, dogs, goats, sheep, horses, monkeys, apes, rabbits, cattle, etc.

As used herein, the term "bioabsorbable polymer" can refer to a polymer whose degradation by-products can be bio-assimilated or excreted via natural pathways in a subject's body.

As used herein, the term "degradable polymer" can refer to a polymer that breaks down into monomers and/or oligomers when placed in a subject's body or in an aqueous solution and maintained under conditions of temperature, osmolality, pH, etc., that mimic physiological media, preferably without involving enzymatic degradation to minimize the risk of triggering the antigen-antibody defense system of the subject.

The present invention relates generally to a method for storing a medical device, and more particularly to a method 10 (FIG. 1) for storing a medical device to substantially preserve the tensile strength of the medical device. Prior art methods for storing medical devices, such as tissue-lined polymeric stents, require submersion in an aqueous preservative solution, such as phosphate buffered saline (PBS) or a glutaraldehyde solution. Storage in such solutions is problematic, however, as the aqueous component of these solutions promotes polymer degradation and thus loss of the stent's tensile strength. Unlike prior art methods for storing medical devices (e.g., polymeric stents), the present invention provides a method 10 for storing a medical device in a hydrophobic liquid (i.e., mineral oil) that does not result in substantial device degradation and loss of tensile strength.

Figure 1:
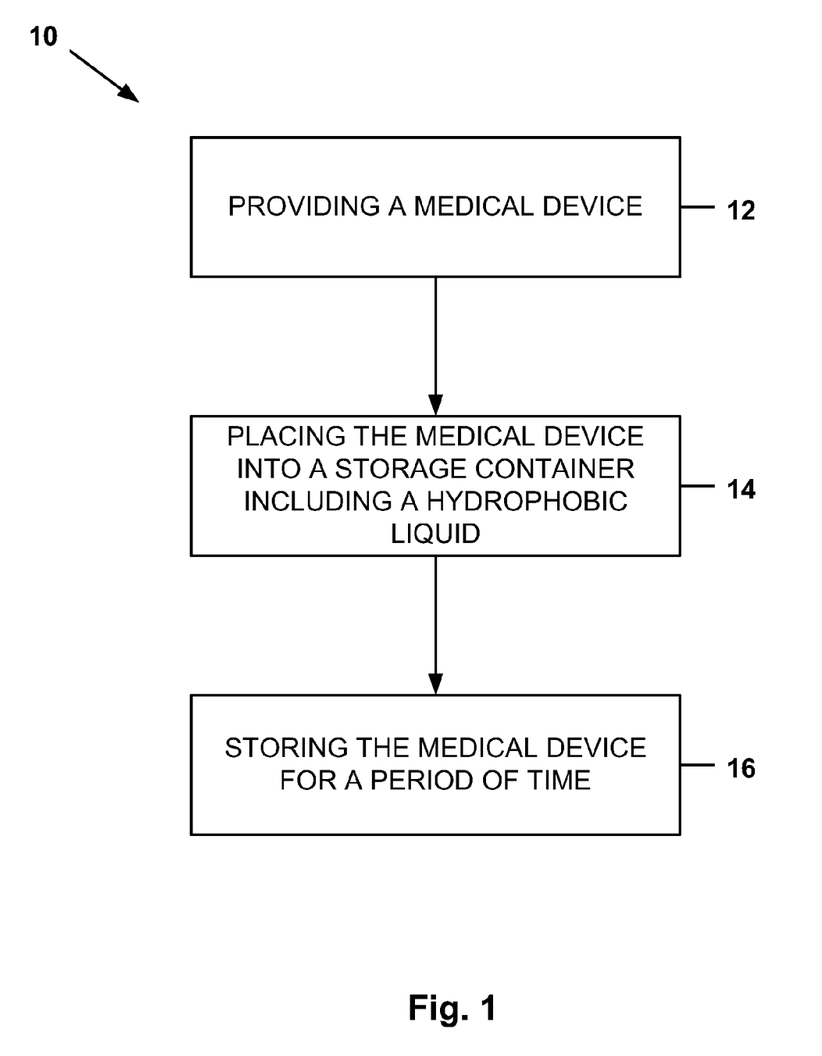
FIG. 1 is a flow diagram illustrating a method for storing a medical device according to one aspect of the present invention.

Referring to FIG. 1, one aspect of the present invention includes a method 10 for storing a medical device (not shown). At Step 12, the method 10 includes providing a medical device having an initial or baseline tensile strength. The medical device can comprise any instrument, implement, machine, contrivance, implant, or other similar or related article, including a component or part, or accessory which is: recognized in the official U.S. National Formulary, the U.S. Pharmacopoeia, or any supplement thereof; intended for use in the diagnosis of disease or other conditions, or in the cure, mitigation, treatment, or prevention of disease, in humans or in other animals; or, intended to affect the structure or any function of the body of humans or other animals.

The medical device can include, for example, endovascular medical devices, such as intracoronary medical devices. Examples of endovascular medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents.

The medical device may also include arterio-venous grafts, by-pass grafts, penile implants, vascular implants and grafts, intravenous catheters, small diameter grafts, artificial lung catheters, electrophysiology catheters, bone pins, needles, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either arterial or venous pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, bandages, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, and cardiac valves.

In one example of the method 10, the medical device can include a bioabsorbable polymeric stent. The bioabsorbable polymeric stent can comprise any expandable lattice or matrix, either alone or in conjunction with a graft material, which is capable of providing support or rigidity to a bodily lumen. The polymeric stent can have a sidewall or sidewalls defining a hollow space or lumen extending therebetween. The cross-sectional shape of the polymeric stent may be generally cylindrical, elliptic, oval, rectangular, triangular, or any other shape. Furthermore, the shape of the polymeric stent may change or be deformable as a consequence of various forces that may press against the polymeric stent.

The polymeric stent can be formed from at least one degradable and bioabsorbable shape memory or oriented polymer (e.g., a thermoplastic polymer, such as a polycarbonate) having a select glass transition temperature (Tg). For example, the at least one degradable and bioabsorbable polymer can have a glass transition temperature of at least about 37° C. (e.g., about 50° C.). The shape memory or oriented polymer can be a homopolymer or copolymer, and can be completely amorphous to minimize the risk of formation of tiny inflammatory crystalline residues during degradation. The chains of the shape memory or oriented polymer are not cross-linked; however, light cross-linking is acceptable provided that thermal and viscoelastic characteristics that allow education, crimping, and deployment of the polymeric stent are maintained.

Examples of the types of shape memory or oriented polymers that may be used to form the polymeric stent can include, but are not limited to, polymers from the linear aliphatic polyester family, such as polylactic acid (PLA), polyglycolic acid (PGA), poliglecaprone, polycaprolactone and their associated copolymers, polycarbonates, polyorthoesters, polyanhydride, polydioxanone (PDS) and polyhydroxybutyrate, polyamides, polyurethanes, polyureas, polyethers, polysaccharides, polyamines, polyphosphates, polyphosphonates, polysulfonates, polysulfonamides, polyphosphazenes, polynorbornene and copolymers of polynorbornene, blends of polybornene with KRATON® (thermoplastic elastomer) and polyethylene, styrenic block copolymer elastomers (e.g., styrene-butadiene), polymethylmethacrylate (PMMA), polyethylene, polyisoprene, copolymers of polylactic acid, copolymers of polyglycolic acid, polyenes, nylons, polycyclooctene, polyvinyl acetate (PVAc), polyvinylidene fluoride (PVDF), blends of polyvinyl acetate/polyvinylidine fluoride (PVAc/PVDF), blends of polymethylmethacrylate/polyvinyl acetate/polyvinylidine fluoride (PVAc/PVDF/PMMA), polyvinylchloride, blends, derivatives, copolymers, and/or combinations thereof.

In one example of the present invention, the polymeric stent can be comprised of poliglecaprone or PDS.

The polymeric stent can be formed by standard techniques, such as extrusion, molding, spinning, injection molding, thermo-formation, film micromachining, laser cutting, or any other processing technique that transforms the shape memory or oriented polymer into a hollow support structure having a matrix or lattice framework. The polymeric stent formed by any one or combination of these processes can be configured to have a final predetermined configuration (e.g., shape, length, thickness, diameter) that is tailored to the application for which the stent is to be utilized. Using injection molding combined with laser cutting, for example, the polymeric stent may be pre-formed to an initial diameter and then heated to a temperature at or above the selected glass transition temperature. The polymeric stent may then be crimped (e.g., using either mechanical means and/or cooling) to a smaller, contracted profile suitable for delivery into a bodily lumen. The polymeric stent can then be cooled and, prior to implantation, and assembled onto a guide catheter (not shown) or other delivery system (e.g., a balloon).

The polymeric stent can be formulated to carry and deliver a variety of materials or therapeutic agents, provided that these materials or agents do not form a solid solution with the shape memory or oriented polymers and do not act as a plasticizer that negatively alters stent functionality. A variety of therapeutic agents can be employed in conjunction with the present invention, including those used for the treatment of a wide variety of diseases and conditions (i.e., the prevention of a disease or condition, the reduction or elimination of symptoms associated with a disease or condition, or the substantial or complete elimination of a disease or condition), such as cardiovascular diseases and cancer.

The materials or agents can be deposited on the exterior or interior surface of the polymeric stent either by physical coupling, impacting, or chemical coupling. Such materials or agents can include pharmaceuticals, pharmaceutically active agents, drugs, genetic agents, non-genetic agents, radiopaque agents, biological tissue(s), and cells.

In one example of the present invention, at least a portion of the polymeric stent can include one or more layers of a biological tissue. The biological tissue layer can line an inner portion of the polymeric stent surface, an outer portion of the polymeric stent surface, and/or a combination thereof. The biological tissue layer can be autologous or allogeneic (e.g., cadaveric or xenogeneic tissue). The biological tissue layer can be derived from any suitable location (e.g., a bodily location), depending upon the intended application of the polymeric stent. For example, the biological tissue layer can be harvested peritoneal fascia tissue, harvested pleural tissue, or harvested pericardial tissue.

The biological tissue layer can be harvested, trimmed, and prepared according to techniques known in the art. For example, the biological tissue layer can be harvested in sheets of appropriate size and then fixed or preserved with alcohol, glutaraldehyde, and/or another biological solution. After being fixed, the biological tissue layer can be trimmed or cut into a desired shape and size. After being trimmed, the biological tissue may be fixed and/or bathed in the biological solution (e.g., to neutralize prions). In one example of the present invention, a layer of biological tissue can be harvested and prepared for attachment to a stent as disclosed in U.S. Pat. No. 7,559,953, the entirety of which is hereby incorporated by reference.

At Step 14, the medical device is placed into a storage container that includes an amount of a hydrophobic liquid. The storage container can comprise any closable or reclosable packaging (e.g., cartons, bottles, cans, etc.) capable of containing, storing, and/or transporting the medical device. The hydrophobic liquid can include any one or combination of liquids that is resistant to or lacks an affinity for water. For example, the hydrophobic liquid can comprise an anhydrous liquid. The anhydrous liquid can include any hydrocarbon-based or petroleum-derived liquid that does not contain any water. For example, the anhydrous liquid can include a paraffinic oil (i.e., based on n-alkanes), a napthenic oil (i.e., based on cycloalkanes), and/or an aromatic oil (i.e., based on aromatic hydrocarbons).

In one example of the present invention, the hydrophobic liquid can comprise sterile mineral oil. Mineral oil or liquid petroleum is a by-product in the distillation of petroleum to produce gasoline and other petroleum-based products from crude oil. Mineral oil is transparent, colorless oil composed mainly of alkanes (typically 15 to 40 carbons) and cyclic paraffins, and related to petroleum jelly (also known as "white petrolatum"). Mineral oil has a density of around 0.8 g/cm$^3$. There are three basic classes of refined mineral oils: paraffinic oils (based on n-alkanes); naphthenic oils (based on cycloalkanes); and aromatic oils (based on aromatic hydrocarbons). Mineral oil of the present invention can include any one or combination of refined mineral oils, as well as other types and classes known in the art.

At Step 16, the medical device is placed into the storage container so that at least a portion of the medical device is immersed in the hydrophobic liquid. For example, a polymeric stent can be placed in the storage container so that the entire polymeric stent is submersed in the hydrophobic liquid. Alternatively, a polymeric stent can be placed in an empty storage container (i.e., one that does not contain hydrophobic liquid). An amount of the hydrophobic liquid can then be added to the storage container so that at least a portion of the polymeric stent is submersed in the hydrophobic liquid.

Once the medical device has been placed into the storage container, the storage container can be sealed and stored for a period of time (e.g., from about 1 week to indefinitely) before removing the medical device from the storage container. Where the medical device is a polymeric stent comprised of poliglecaprone, for example, the polymeric stent can be stored in sterile mineral oil for a period of about 2 weeks to about 4 weeks. Alternatively, where the medical device is a polymeric stent comprised of PDS, the polymeric stent can be stored in sterile mineral oil for a period of about 8 weeks. Advantageously, storage of the medical device in a hydrophobic liquid substantially preserves the initial tensile strength of the device. By "substantially preserve", it is meant that upon removal of the medical device from the hydrophobic liquid, the tensile strength of the device is at least about 50 percent, at least about 60 percent, at least about 70 percent, at least about 80 percent, or at least about 90 percent of the medical device's initial tensile strength.

After the period of time, the medical device can be removed from the storage container and implanted in or on a subject to treat any one or combination of diseases or conditions. Where the medical device comprises a bioabsorbable polymeric stent, for example, the polymeric stent can be implanted into a bodily lumen to treat, e.g., stenosis or a vulnerable plaque. Examples of bodily lumens or passageways into which the polymeric stent can be implanted include the gastrointestinal tract (e.g., bile ducts, colon, duodenum), esophagus, trachea, urinary tract (e.g., urethra, prostate), and vasculature (e.g., renal arteries, coronary blood vessels, peripheral blood vessels, intracranial blood vessels). The polymeric stent can be introduced into the bodily lumen or passageway using a guide catheter, for example, and then advanced to a target site within the bodily lumen (e.g., the site of stenosis or a vulnerable plaque).

After the polymeric stent is positioned at the target site within the bodily lumen, the stent may be expanded into its final predetermined shape. The polymeric stent can be expanded using any one or combination of known techniques, such as via a balloon, inflation fluid, and/or the bodily heat of the subject. For example, the polymeric stent can be expanded using a combination of sustained balloon expansion and memory recovery (i.e., as the select Tg of the stent is reached). Storage of the polymeric stent in the hydrophobic liquid (i.e., sterile mineral oil) prevents or mitigates stent degradation and loss of tensile strength that typically occurs during storage in aqueous solutions. Consequently, the polymeric stent is better able to resist fatigue caused by intraluminal forces (e.g., torsion, compression, extension and flexion) upon implantation in a bodily lumen.

The following example is for the purpose of illustration only and is not intended to limit the scope of the claims, which are appended hereto.

EXAMPLE

The purpose of this experiment was to test degradation patterns of various bioabsorbable materials in several different media.

Tensile Testing

The following bioabsorbable materials were tested: PLA; PLG; PDS; polyglactin (VICRYL); poliglecaprone (MONOCRYL); chromic catgut; and polyprolene (as a non-absorbable control). Five samples of equal length (20 mm) and diameter (2.4 mm) of each material were prepared by immersion in PBS, mineral oil, and 0.625% glutaraldehyde and incubated at 37° C. Mineral oil was chosen as an anhydrous solute as most bioabsorbable polymer degradation is stimulated by aqueous solutions. Samples were incubated for 1, 2, 3, 4 and 8 weeks.

Figure 2:
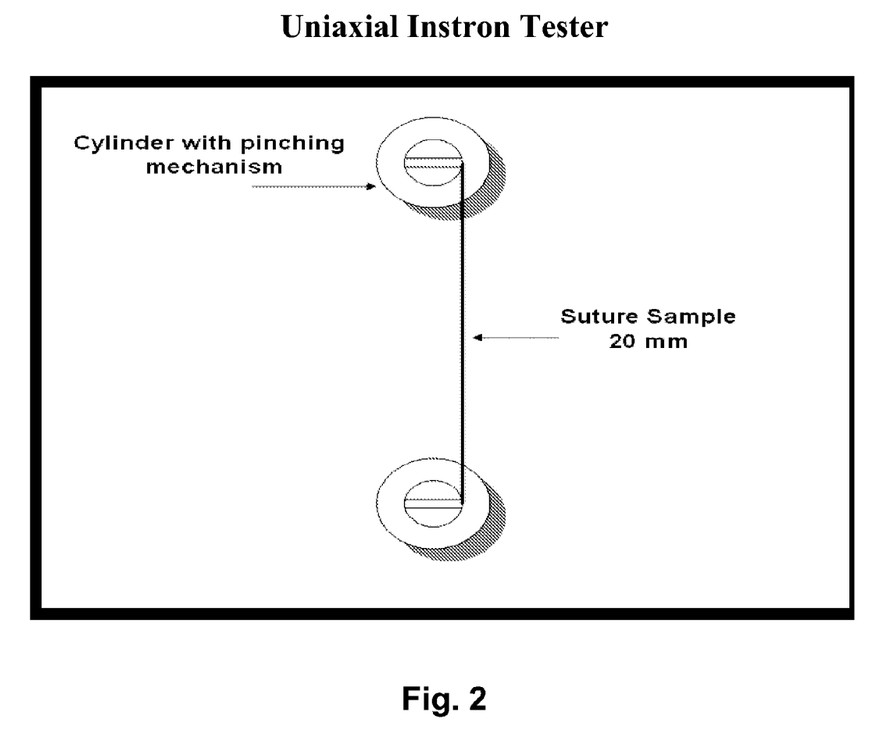
FIG. 2 is a schematic illustration of a uniaxial, unidirectional testing machine.

Tensile testing was done at the Cleveland Clinic Lerner School of Medicine Department of Biomedical Engineering Core Testing facility. A uniaxial, unidirectional testing machine (INSTRON, Norwood, Mass.) (FIG. 2) was used to perform tensile testing at time 0, 1, 2, 3, 4, and 8 weeks. The samples were secured around cylinders, and the distance between the hooks of the cylinders was fixed at 20 mm for all samples. All specimens were serialized for each load, and data were recorded. The specimens were loaded at a slow controlled rate of 1 mm/sec and original length of 20 mm. The data was processed to determine breaking force (N) (the failure load at which the material breaks) and stiffness (N/mm) (the slope of force-elongation curve).

Statistical Analysis

The mean and standard error of each material and solution tested were calculated, and a linear repeated measure ANOVA model was fit to the data. An unstructured covariance structure was used to adjust for the unequally spaced repeated measurements on each sample. To evaluate the relationship between all solution and material combinations, comparisons were made at each time point using two-sided t-tests. Adjusted means and standard errors from these models were also calculated. A Bonferroni corrected significance criterion of 0.0002 was used to compare all possible combinations at each time point. Analysis was performed using SAS software (version 9.1) (Cary, N.C.).

Results

Table 1 summarizes the baseline breaking forces for each material. Poliglecaprone had the greatest baseline breaking force at 48.56±1.35 (N) (p<0.0001).

TABLE 1

Baseline summary of breaking force comparison among 7 materials

| Materials | PLA | PLG | Prolene | Chromic | Polydioxanone | Polyglactin | Poliglecaprone |
|---|---|---|---|---|---|---|---|
| Breaking Force (N) Mean (SEM) | 10.15 (1.35) | 10.95 (1.35) | 27.41 (1.35) | 35.56 (1.35) | 40.72 (1.34) | 40.34 (1.35) | 48.56 (1.35) |
| P value < 0.0002 | | | | | | | |

(Solid lines join the groups with no significant difference in the values).

Figure 3:
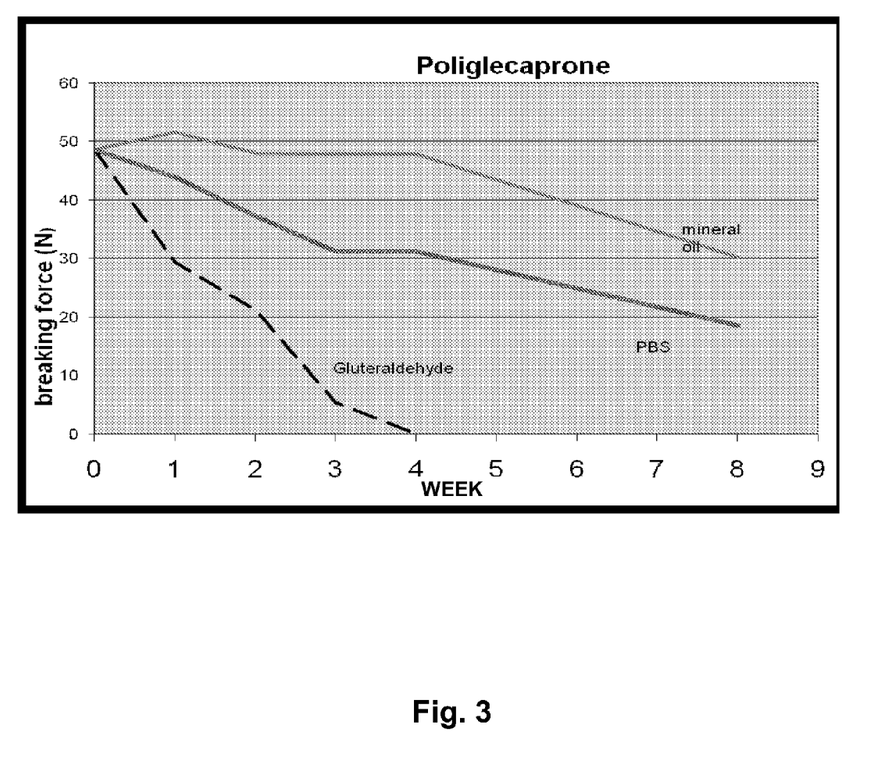
FIG. 3 is a plot of breaking force (N) versus time (weeks) showing the tensile strength of poliglecaprone in mineral oil, phosphate buffered saline (PBS), and 0.625% glutaraldehyde solution.
Figure 4:
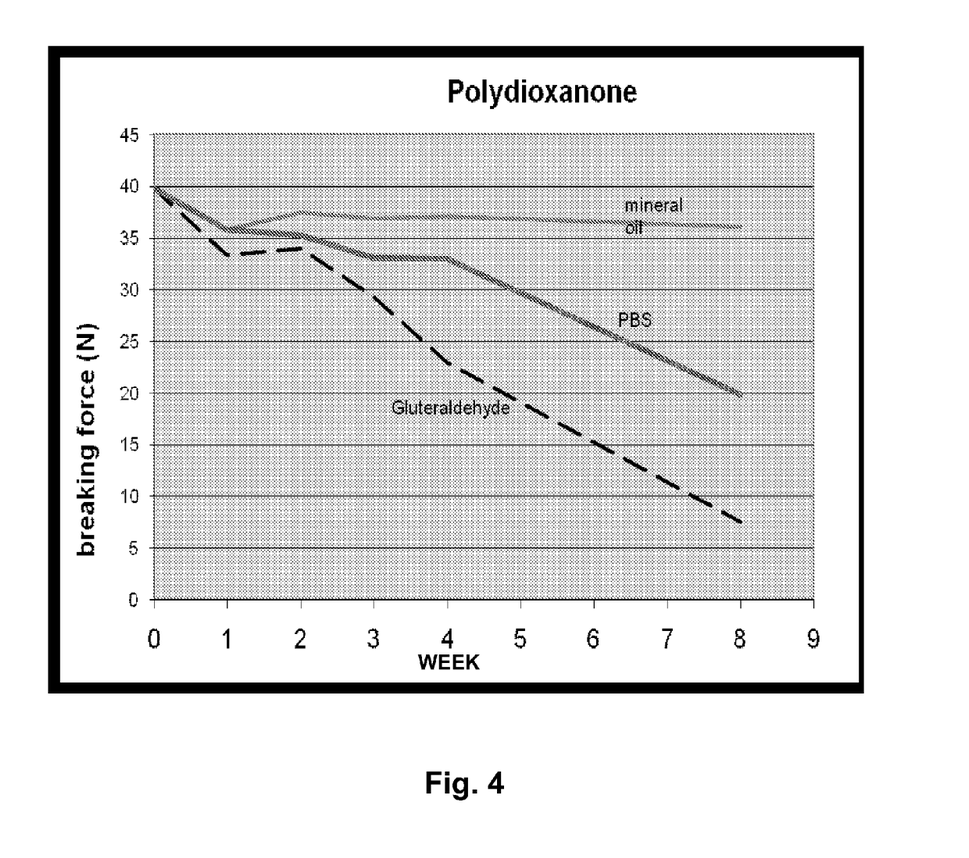
FIG. 4 is a plot of breaking force (N) versus time (weeks) showing the tensile strength of polydioxanone in mineral oil, PBS, and 0.625% glutaraldehyde solution.
Figure 5:
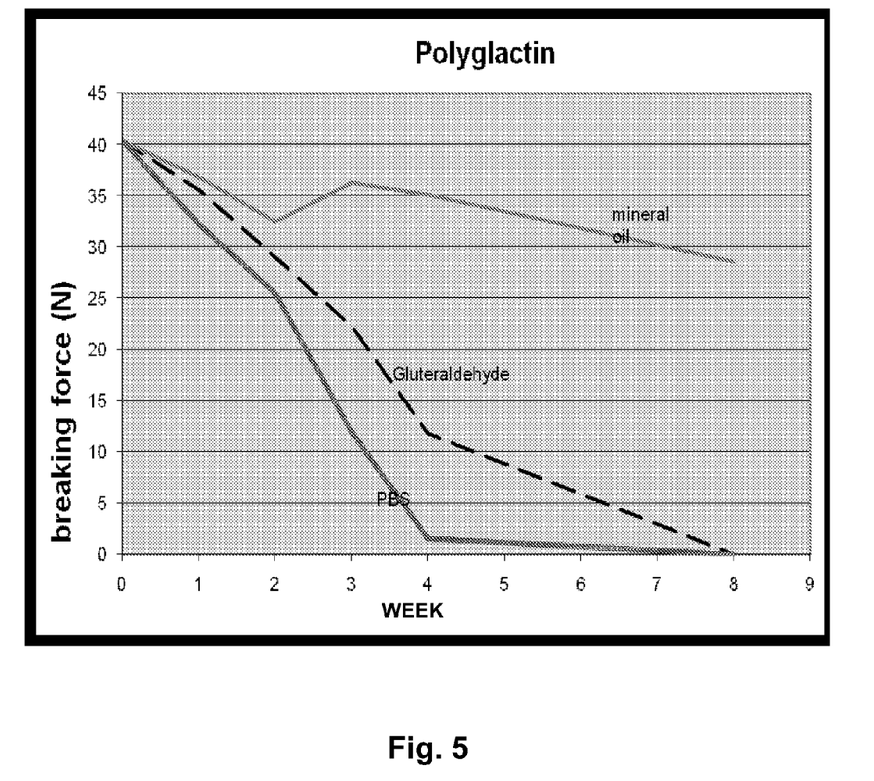
FIG. 5 is a plot of breaking force (N) versus time (weeks) showing the tensile strength of polyglactin in mineral oil, PBS, and 0.625% glutaraldehyde solution.
Figure 6:
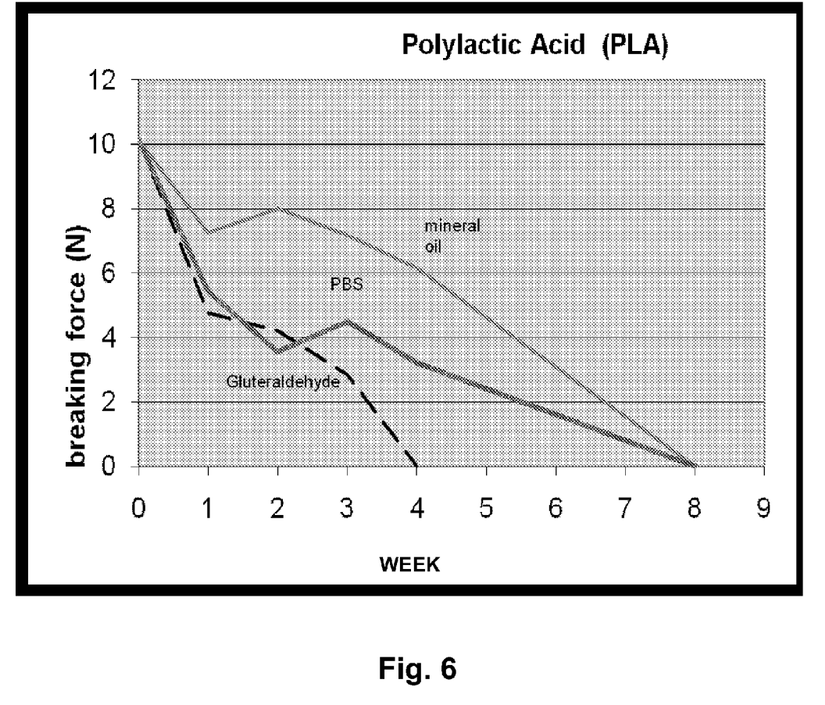
FIG. 6 is a plot of breaking force (N) versus time (weeks) showing the tensile strength of polylactic acid in mineral oil, PBS, and 0.625% glutaraldehyde solution.
Figure 7:
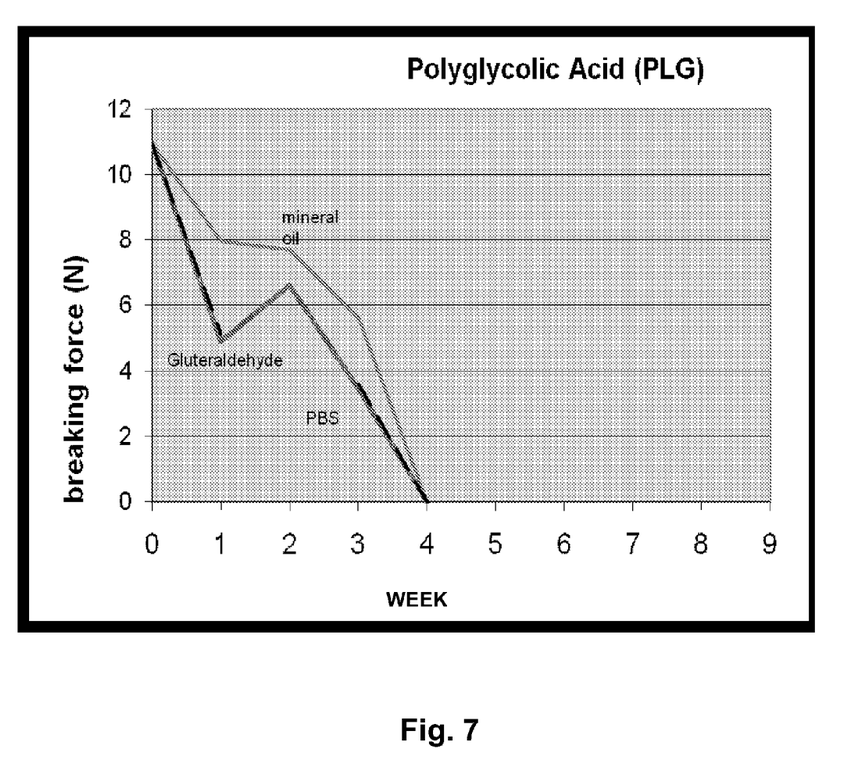
FIG. 7 is a plot of breaking force (N) versus time (weeks) showing the tensile strength of polyglycolic acid in mineral oil, PBS, and 0.625% glutaraldehyde solution.
Figure 8:
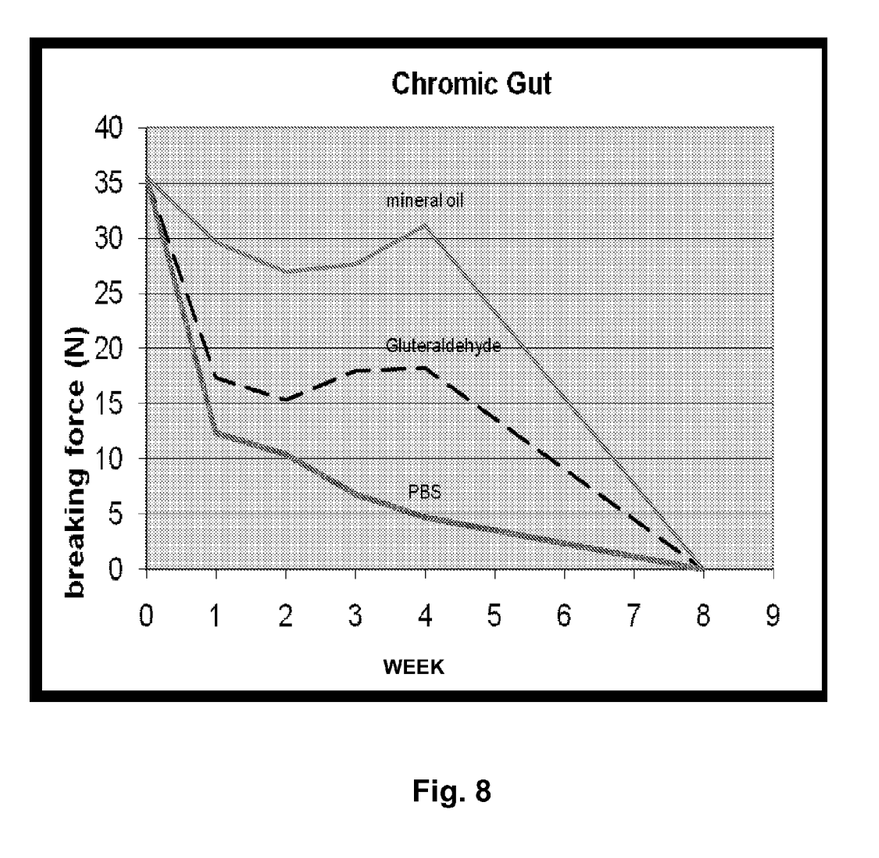
FIG. 8 is a plot of breaking force (N) versus time (weeks) showing the tensile strength of chromic catgut in mineral oil, PBS, and 0.625% glutaraldehyde solution.
Figure 9:
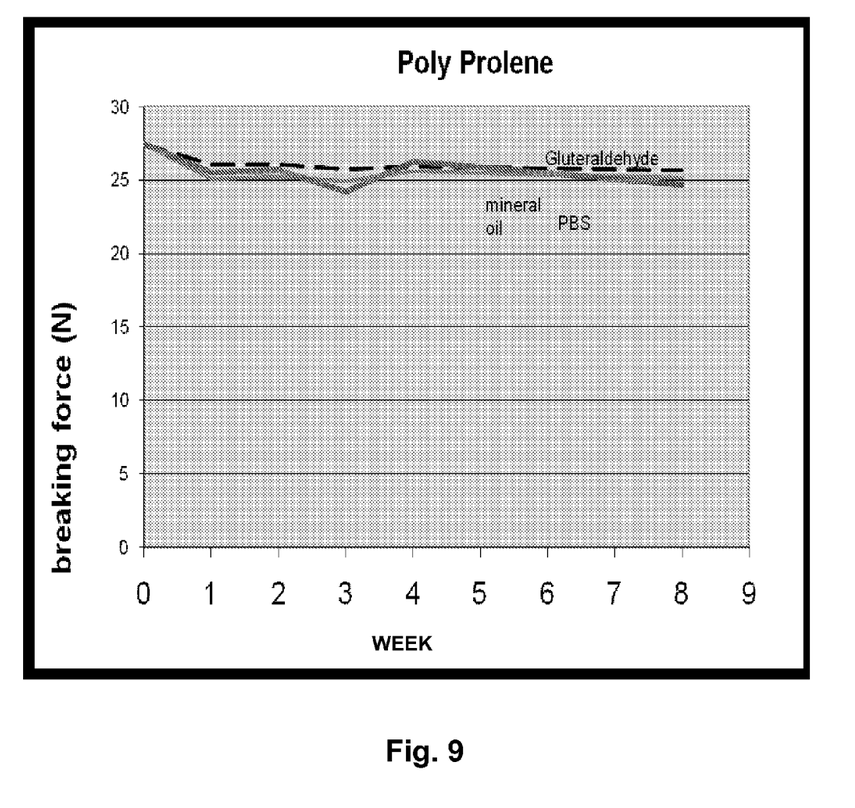
FIG. 9 is a plot of breaking force (N) versus time (weeks) showing the tensile strength of polyprolene in mineral oil, PBS, and 0.625% glutaraldehyde solution.

After emersion in the various solutions, poliglecaprone (FIG. 3) in mineral oil had the greatest breaking force at week 1. Similar results were also observed at week 2 and week 4. At 4 weeks, poliglecaprone (FIG. 3), PDS (FIG. 4), and polyglactin (FIG. 5) in mineral oil all had similar strengths and were not statistically different from one another. However, at 8 weeks, PDS in mineral oil was associated with the strongest tensile profile with breaking forces at 36.13±0.35 (N). Based on these outcomes, it appears that early on poliglecaprone in mineral oil is associated with the greatest breaking force, but at later periods, PDS in mineral oil provides the stronger tensile profile. Other substances tested are also depicted as follows: PLA (FIG. 6); PLG (FIG. 7); chromic catgut (FIG. 8); and polyprolene (FIG. 9).

Over the entire 8 weeks, all materials except polyprolene and the PDS in mineral oil showed significant decreases in strength (Table 2). With PLA and PLG, emersion in glutaraldehyde and PBS solutions resulted in similar breaking forces over the entire 8 weeks (p=0.021 and p=0.97). All other comparisons were statistically significant (Table 2).

TABLE 2

Summary of breaking forces over 8 weeks for each material in various solutions

| Material | Solution | Decreasing Trend | P-Value | Similarities |
|---|---|---|---|---|
| Chromic | Glutaraldehyde | <0.0001 | <0.0001 | |
| | PBS | <0.0001 | | |
| | Mineral oil | <0.0001 | | |
| Monocryl | Glutaraldehyde | <0.0001 | <0.0001 | |
| | PBS | <0.0001 | | |
| | Mineral oil | <0.0001 | | |
| PDS | Glutaraldehyde | <0.0001 | <0.0001 | |
| | PBS | <0.0001 | | |
| | Mineral oil | 0.12 | | |
| PLA | Glutaraldehyde | <0.0001 | <0.0001 | ▓ |
| | PBS | <0.0001 | | |
| | Mineral oil | <0.0001 | | |
| PLG | Glutaraldehyde | <0.0001 | <0.0001 | ▓ |
| | PBS | <0.0001 | | |
| | Mineral oil | <0.0001 | | |
| Prolene | Glutaraldehyde | 0.88 | 0.27 | ▓ |
| | PBS | 0.69 | | |
| | Mineral oil | 0.30 | | |
| Vicryl | Glutaraldehyde | <0.0001 | <0.0001 | |
| | PBS | <0.0001 | | |
| | Mineral oil | <0.0001 | | |

(Gray lines join the groups with no significant difference in the values).

From the above description of the invention, those skilled in the art will perceive improvements, changes and modifications. Such improvements, changes, and modifications are within the skill of the art and are intended to be covered by the appended claims.

Having described the invention, the following is claimed:

1. A method for storing a medical device, said method comprising the steps of:
   providing a medical device having an initial tensile strength, wherein at least a portion of the medical device is bioabsorbable;
   placing the medical device into a storage container so that at least a portion of the medical device is immersed in a hydrophobic liquid capable of substantially preserving the initial tensile strength of the medical device over a period of time;
   storing the medical device in the storage container for the period of time.

2. The method of claim 1, wherein the medical device is a polymeric stent.

3. The method of claim 2, wherein the polymeric stent is comprised of at least one polymer selected from the group consisting of poliglecaprone, polydioxanone (PDS), polyglactin, chromic catgut, polylactic acid (PLA), and poly(lactic-co-glycolic acid) (PLG).

4. The method of claim 3, wherein the at least one polymer includes PDS.

5. The method of claim 1, wherein the hydrophobic liquid is a hydrocarbon-based liquid or a petroleum-derived liquid.

6. A method for storing a medical device, said method comprising the steps of:
   providing a medical device having an initial tensile strength, at least a portion of the medical device being bioabsorbable;
   placing the medical device into a storage container so that at least a portion of the medical device is immersed in an anhydrous liquid capable of substantially preserving the initial tensile strength of the medical device over an extended period of time;
   storing the medical device in the storage container for the extended period of time; and
   removing the medical device from the storage container.

7. The method of claim 6, wherein the medical device is a polymeric stent.

8. The method of claim 7, wherein the polymeric stent is comprised of poliglecaprone, polydioxanone (PDS), polyglactin, chromic catgut, PLA and PLG.

9. The method of claim 8, wherein the at least one polymer includes PDS.

10. The method of claim 7, wherein at least a portion of the polymeric stent is lined with a biological tissue.

11. A method for storing a bioabsorbable PDS stent, said method comprising the steps of:
    providing a bioabsorbable PDS stent having an initial tensile strength;
    placing the PDS stent into a storage container so that at least a portion of the PDS stent is immersed in sterile mineral oil;
    storing the PDS stent in the storage container for an extended period of time; and
    removing the PDS stent from the storage container;
    wherein the initial tensile strength of the PDS stent is substantially preserved over the extended period of time.

12. The method of claim 11, wherein at least a portion of the PDS stent is lined with a biological tissue.

* * * * *